US011602582B2

United States Patent
Krzysik

(10) Patent No.: US 11,602,582 B2
(45) Date of Patent: Mar. 14, 2023

(54) INTIMATE CARE LUBRICANT COMPOSITIONS AND METHODS FOR MAKING SAME

(71) Applicant: Chemsil Silicones, Inc., Chatsworth, CA (US)

(72) Inventor: Duane Krzysik, Salisbury, NC (US)

(73) Assignee: Chemsil Silicones, Inc., Chatsworth (CA)

( * ) Notice: Subject to any disclaimer, the term of this patent is extended or adjusted under 35 U.S.C. 154(b) by 368 days.

(21) Appl. No.: 15/949,889

(22) Filed: Apr. 10, 2018

(65) Prior Publication Data
US 2019/0307927 A1 Oct. 10, 2019

(51) Int. Cl.
| | | |
|---|---|---|
| A61L 31/06 | (2006.01) |
| C10M 107/50 | (2006.01) |
| C10M 107/34 | (2006.01) |
| C10M 119/26 | (2006.01) |
| C10M 135/08 | (2006.01) |
| C10M 173/02 | (2006.01) |
| C10M 169/00 | (2006.01) |
| C10N 40/00 | (2006.01) |
| C10N 50/00 | (2006.01) |

(52) U.S. Cl.
CPC .......... *A61L 31/06* (2013.01); *C10M 107/34* (2013.01); *C10M 107/50* (2013.01); *C10M 119/26* (2013.01); *C10M 135/08* (2013.01); *C10M 173/02* (2013.01); *A61L 2400/10* (2013.01); *C10M 169/00* (2013.01); *C10M 2201/02* (2013.01); *C10M 2209/1045* (2013.01); *C10M 2219/042* (2013.01); *C10M 2221/02* (2013.01); *C10M 2229/025* (2013.01); *C10N 2040/50* (2020.05); *C10N 2050/013* (2020.05)

(58) Field of Classification Search
CPC ...... A61L 31/06; A61L 2400/10; A61L 31/14; A61L 2300/404; A61L 2300/43; A61L 2300/452; A61L 2300/802; C10M 107/50; C10M 107/34; C10M 119/26; C10M 135/08; C10M 173/02; C10M 169/00; C10M 2201/02; C10M 2209/1045; C10M 2219/042; C10M 2221/02; C10M 2229/025; C10N 2040/50; C10N 2050/013; A61K 9/0034; A61K 8/068; A61K 8/89; A61K 9/1075; A61K 47/34; A61Q 19/00

See application file for complete search history.

(56) References Cited

U.S. PATENT DOCUMENTS

| | | | |
|---|---|---|---|
| 4,874,547 A * | 10/1989 | Narula ....................... | C08J 3/03 |
| | | | 516/76 |
| 5,885,591 A | 3/1999 | Ahmad et al. | |
| 5,925,338 A | 7/1999 | Karassik et al. | |
| 6,139,848 A | 10/2000 | Ahmad et al. | |
| 6,419,909 B1 | 7/2002 | Lorant et al. | |
| 7,285,517 B2 | 10/2007 | Ahmad et al. | |
| 7,405,186 B2 | 7/2008 | Harrison | |
| 8,486,872 B2 | 7/2013 | Morrison et al. | |
| 9,456,921 B2 | 10/2016 | Harrison et al. | |
| 9,474,768 B1 | 10/2016 | Richards et al. | |
| 2003/0040572 A1 | 2/2003 | Marteaux et al. | |
| 2008/0050398 A1 | 2/2008 | Bockmeuhl et al. | |
| 2008/0152680 A1 | 6/2008 | Brown et al. | |
| 2010/0137454 A1* | 6/2010 | Barmes .................. | C11D 3/373 |
| | | | 514/772.3 |
| 2011/0300083 A1* | 12/2011 | Yontz ..................... | A61P 31/10 |
| | | | 424/769 |
| 2012/0294820 A1 | 11/2012 | Harrison et al. | |
| 2014/0022701 A1* | 1/2014 | Machida .................. | H01G 9/15 |
| | | | 428/419 |
| 2016/0251596 A1 | 9/2016 | Valencia Sil et al. | |
| 2017/0281657 A1 | 10/2017 | Buckheit, Jr. et al. | |

FOREIGN PATENT DOCUMENTS

| | | | | |
|---|---|---|---|---|
| GB | 2079300 | * | 7/1980 | ............. C08L 83/04 |
| WO | 2014152154 A1 | | 9/2014 | |

OTHER PUBLICATIONS

International Search Report and Written Opinion, International Application No. PCT/US19/20899, dated Jun. 7, 2019.
Sun et al., J. Cosmet. Sci. 56,253-265. (Jul./Aug. 2005).
Extended European Search Report application No. PCT/US2018020899, dated Jan. 14, 2022.

* cited by examiner

*Primary Examiner* — Matthew P Coughlin
*Assistant Examiner* — Thurman Wheeler
(74) *Attorney, Agent, or Firm* — Carlos A. Fisher; Stout, Uxa & Buyan, LLP

(57) ABSTRACT

Silicone-in-water emulsions and methods for making same, are disclosed which are useful and effective as lubricants for use in intimate care applications, as a skin condition, as a surgical lubricant and/or as a carrier for an active topical pharmaceutical agent. In preferred examples, the emulsions of the present invention are flowable, have a viscosity of equal to or below about 15,000 centipoise (cP), and are stable upon storage for at least about 1 year.

21 Claims, No Drawings

INTIMATE CARE LUBRICANT COMPOSITIONS AND METHODS FOR MAKING SAME

FIELD OF THE INVENTION

The present invention relates to compositions and methods of making stable compositions suitable for use as lubricants for use in in personal care applications; for example, and without limitation, applications in which one or more body parts are lubricated, protected from harm, and/or provided a more pleasurable experience during sexual activity. In other applications, the invention may have other uses; for example, as a surgical lubricant, a personal lubricant to prevent skin chafing, as a skin conditioner, and/or as a vehicle for the topical delivery of drugs.

BACKGROUND AND SUMMARY

Lubrication is defined herein as the separation of surfaces, otherwise in contact with each other, by a lubricant such that when the surfaces are in motion relative to each other the lubricant reduces frictional resistance associated with such motion, relative to the frictional resistance in the same system when the lubricant is absent. Lubrication tends to prevent or lessen wear, irritation, heat generation, and/or damage to the surfaces due to such motion.

Personal lubricants in the form water-soluble, pourable low viscosity thixotropic gels, water-soluble jellies and the like, are known and are useful for providing lubricity to various parts of the human body, for example, to mucous membranes, such as the oral, rectal, vaginal and other mucosa. For example, see Ahmad et al U.S. Pat. No. 5,885,591. Certain such lubricants have been proposed which may generate soothing heat or warming when placed in contact with the human body. See also, Harrison, J., U.S. Pat. No. 7,405,186.

Additional personal lubricants have been discussed in e.g., Ahmad et al., U.S. Pat. No. 6,139,848; Ahmad et al., U.S. Pat. No. 7,005,408; Ahmad et al., U.S. Pat. No. 7,285,517; and Harrison, U.S. Pat. No. 7,405,186. These are all single phase water-soluble lubricants lacking a silicone component. Single phase water-soluble lubricants tend to be tacky or stringy as they dry and often lack a sufficiently high degree of lubricity.

On the other hand, single phase silicone lubricants may often offer superior lubrication or lubricity, but are notorious for generally staining fabrics, such as cotton, polyester or satin, and removal of the stain is usually difficult or impossible. Such lubricants can feel greasy and can be difficult to clean up. Further, silicone can be difficult to wash from a user's skin as well as from fabrics.

Silicone and water-soluble fluid phases are immiscible. Therefore, formation of an emulsion is necessary to take advantage of the properties of each of these phases in a single composition. Generally emulsions between two immiscible substances are substantially opaque "white" substances due to the admixture of droplets of, for example, oil (such as silicone oil) and of the aqueous phase, each having a different refractive index. In such cases, the different refractive indices of the immiscible phases tend to cause opacity and cloudiness.

However, opaque or cloudy personal lubricants, particularly those used as intimate care lubricants or sexual lubricants are widely considered to be aesthetically unpleasing and may be commercially unsuccessful because of this, despite any advantageous physical properties.

Clarification of cosmetic emulsions has generally involved using one of two possible approaches: a) the formation of microemulsions or b) matching of refractive indices. See e.g. Sun et al., J. Cosmet. Sci. 56, 253-265 (July/August 2005). The formation of microemulsions generally involves the use of high concentrations of surfactant emulsifiers to compete for limited amounts of a non-water miscible phase. The formation of microemulsions often occurs spontaneously upon combination of the emulsion components despite the popularly used term "microemulsion". This forces the average droplet size of such emulsions to be very small (less than 99 nm in diameter). When the droplet size is less than the wavelengths of visible light, the emulsion will appear clear. However, the high concentrations of surfactants required to stabilize the emulsion can render these microemulsions irritating to sensitive skin.

When using the technique of refractive index matching to clarify a mixture of immiscible liquids, generally the formulation is determined empirically and the methodology used in one instance is often not generally applicable, for example, to all or even most other formulations. In one reference, an antiperspirant composition is made using silicone oil and an aqueous liquid with no reference to methodology, theoretic basis, or examples of refractive indices. See Karassik et al., U.S. Pat. No. 5,925,338. Harrison, et al., U.S. Pat. No. 9,456,921 discusses refractive index-matched personal lubricant compositions. Brown, U.S. Patent Publication 2008/0152680 discusses methods of making cosmetic formulations containing, as a separate phase, a fractal gel network formed of insoluble fractal particles comprising metal oxides of opposite charges, in which a polymer is used to match the refractive index of one of the insoluble, undilutable fractal particles. Lorant et al. (U.S. Pat. No. 6,419,909) discusses cosmetic emulsions in which the refractive index of a hydrophobic phase is adjusted to increase transparency by substantially matching the aqueous phase. Bockmeuhl et al. U.S. Patent Publication No. US 2008/0050398 discloses compositions for the topical delivery of a specific peptide (β-defensin 2) to the skin. The compositions are preferably cosmetic, water treatment, or pharmaceutical compositions. The compositions of Bockmeuhl et al. do not include personal lubricants.

Single phase silicone personal lubricants are described in Fevola et al., Cosmetics and Toiletries, 123; 6, 59-68 (June 2008). Such personal lubricants are described as being very lubricous, but cleanup is difficult since these personal lubricants are water insoluble, and tends to stain fabrics such as clothing and bedclothes. A lubricant in a skin conditioner, particularly skin conditioners containing silicone, can give a smooth, silky feeling to dry, chapped skin.

Osmolality is defined as the number of osmoles of a solute per unit total weight of the solute and solvent. This can be measured upon the dissociation of an ionic compound into its constituent ions in solution. Recent studies have suggested that intimate care lubricants with a high osmolality might cause health or safety issues such as, for example, vaginal and/or epithelial damage. Epithelial damage, could in turn, increase infection risks, for example, by HIV and other sexually transmitted infections.

Anhydrous silicone lubricants have very low aqueous solubility (typically measured in parts per million) and therefore have very low osmolality, but are considerably more expensive than the above noted group of materials. One way to reduce the osmolality of water-soluble personal lubricants is to create emulsions containing water, glycols/glycerin and silicone materials. However, these emulsions require high viscosity in order to obtain acceptable stability and are therefore less than ideal in terms of ease of use and comfort during use as a personal lubricant.

In one example the present invention is directed to a method of making a stable low-viscosity, substantially clear or translucent lubricant composition comprising:

a) mixing a non-solid silicone lubricant and at least one non-solid non-ionic surfactant component to form a silicone phase;

b) mixing, in a separate vessel, water and at least one glycol to form an aqueous phase;

c) mixing a rheology modifier with either said aqueous phase or said silicone phase;

d) slowly adding water or a portion of said aqueous phase with gentle mixing to the silicone phase to form a water-in-silicone emulsion;

e) combining the aqueous phase and the viscous water-in-silicone emulsion with mixing for a sufficient time to invert the viscous water-in-silicone emulsion to a silicone-in-water emulsion, thereby forming a stable, low-viscosity, silicone-in-water lubricant composition; and f) optionally mixing an effective amount of a refractive index (RI) adjusting agent ("RIAA") with the low viscosity, clear silicone-in-water lubricant emulsion composition to obtain a substantially clear or translucent emulsion.

In another example the present invention is directed to a stable, low-viscosity, substantially clear or translucent silicone-in-water emulsion composition comprising:

about 0.1% to about 1% by weight of a rheology modifier,
about 1% to about 6% by weight of a non-ionic surfactant component;
about 15% to about 60% by weight of one or more silicone lubricants; and
an amount of one or more water-miscible RIAA sufficient to render the composition substantially clear or translucent; the low-viscosity, substantially clear or translucent silicone-in-water emulsion composition being stable for at least about 1 year at room temperature and effective as a lubricant suitable for use in intimate care applications.

In another example the present invention is directed to a condom product in which the inside surface, the outside surface, or both the inside surface and the outside surface of the condom are treated with a stable, low-viscosity, substantially clear or translucent silicone-in-water emulsion composition comprising:

about 0.1% to about 1% by weight of a rheology modifier,
about 1% to about 6% by weight of a non-ionic surfactant component;
about 15% to about 60% by weight of one or more silicone lubricants; and
an amount of one or more water-miscible RIAA sufficient to render the composition substantially clear or translucent; the low-viscosity, substantially clear or translucent silicone-in-water emulsion composition being stable for at least about 1 year at room temperature and effective as a lubricant suitable for use in intimate care applications.

By referring to emulsion "stability" or using the words "stability", "stable" or "stabilize" with regard to emulsions, is meant the ability of an emulsion, once formed, to resist changes in its physiochemical properties with time.

Instability of multiphase silicone-containing lubricant emulsions is a common problem, wherein the density or specific gravity of the silicone phase (for example, between about 0.85-0.95) and the density or specific gravity of the water-soluble phase, for example, between 1.0-1.5, are different. This density difference between the silicone phase and the water phase can cause unwanted formulation instability, for example, "creaming", in which the droplets are less dense than the continuous phase and move upward; "sedimentation", in which the droplets are more dense than the continuous phase and move downward; "flocculation" of multiple droplets, "coalescence" of droplets to form larger drops; and phase inversion, in which, for example, a "silicone in water" emulsion becomes a "water in silicone" emulsion. These are all forms of emulsion instability. An example of lack of emulsion stability is separation of the phases over a time period, such as a time period of six months or greater, or 1 year or greater, or 2 years or greater. High emulsion stability over at least 1 year, or at least 2 years, is an indication of 'acceptable" shelf life.

Problematically, however, low viscosity emulsions have been considered notoriously difficult to stabilize.

In the present application unless otherwise indicated, each and every range of values (concentrations, viscosities, and the like) stated in this specification, including the claims, are intended to specifically include every point and subrange within the entire expressly specified range and not just the endpoint(s). For example, a range stated to be 0 to 10 is intended to disclose all whole numbers between 0 and 10 such as, for example 1, 2, 3, 4, etc., all fractional numbers between 0 and 10 to three significant figures, for example 1.5, 2.3, 4.57, etc., and the endpoints 0 and 10, as well as all subranges having these numbers as endpoints (such as the subranges "3 to 5" and "2.30 to 7.13"). Similarly, ranges expressed as "greater than" (or less than) a given value means the range of values extending between that value and the highest value possible (or lowest value possible) in the specific context, such as 100% (or 0%) when expressed as a percentage, and also includes all whole and fractional numbers to three significant figures between the given value and the highest (or lowest) possible value. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

In the present application by "low viscosity" is meant having a viscosity equal to or below about 15,000 centipoise (cP), or below about 12,000 cP, preferably equal to or below about 10,000 cP. In some compositions, such as liquid lubricant compositions, a low viscosity composition has a viscosity within the range of from about 150 cP, or about 100 cP, to about 15000 cP. Preferably the viscosity of the present compositions is between about 150 cP to about 10,000 cP, or from about 150 cP to about 7000 cP, or from about 1000 cP to about 10,000 cP, or about 2000 cP to about 10,000 cP, or about 3000 cP; in each case.

In the present application, by "non-ionic surfactant" is meant an uncharged amphiphilic compound, having a hydrophilic but uncharged "head" portion and a hydrophobic "tail" portion. Examples of types of non-ionic surfactants include, without limitation: polyalkylene glycol alkyl ethers; glucoside alkyl ethers; polyethylene glycol alkylphenyl ethers, glycerol alkyl esters; polyoxyethylene glycol sorbitan alkyl esters; sorbitan alkyl esters; alkylamide ethanolamines; alkane alkylamine oxides; block copolymers of polyethylene glycol and polypropylene glycol; polyethoxylated fatty acid amines and ethoxylated aliphatic alcohols. Preferred non-ionic surfactants are the ethoxylated fatty alcohols.

Examples of specific non-ionic surfactants are well known, and include, without limitation: alkyl polyglucoside; Brij 4™ surfactants; Brij™ 35; Cetomacrogol™ 1000, C11-15 Pareth-7, Trideceth-6; decyl glucoside; decyl polyglucose; glycerol monostearate; IGEPAL™ CA-630; isoceteth-20; lauryl glucoside; maltosides; monolaurin; mycoosubtilin; narrow-range ethoxlate; Nonidet™ P-40; nonoxynols; NP™-40; octaethylene glycol monodoceyl ether; N-octyl beta D-thioglucopyranoside; octyl glucoside; oleyl alcohol; PEG-10 sunflower glycerides; pentaethylene glycol monodecyl ether; polidocanol; poloxamers; poloxamer 407; polyethoxylated tallow amine; polyglycerol polyricinoleate; polysorbate; polysorbate 20; polysorbate 80; sorbitan; sorbitan monolaurate; sorbitan monostearate; sorbitan tristearate; stearyl alcohol; surfactin; Tritons; Triton™ X-100; Tween™; Tween™ 80.

Instability of multiphase silicone-containing lubricant emulsions is particularly common, wherein the density or specific gravity of the silicone phase (for example, between about 0.85-0.95) and the density or specific gravity of the water-miscible phase (for example, between 1.0-1.5) are radically different. As described above, this density difference between the silicone phase and the water phase can cause unwanted formulation instability, for example, creaming, sedimentation, flocculation, and coalescence or phase inversion.

As used in this application a "rheology modifier" is a chemical agent used to control the emulsion viscosity. Rheology modifiers may be Newtonian or pseudoplastic, thixotropic, etc.; such thickeners may have no other function in an emulsion formulation than to thicken or may have, without limitation, additional activities such as an emulsifying activity, a buffering activity, a surfactant activity, and/or an amphiphilic property. The addition of a rheology modifier may also aid in improving emulsion stability when included in a silicone and water emulsion.

Thus, there continues to be a need for stable, low viscosity lubricating emulsion compositions containing silicones suitable for use in intimate care applications combined with an aqueous phase. Preferably such emulsion compositions have similar relatively low viscosity and rheology as single phase glycol-based lubricants and single phase silicone lubricants, are easy to apply during use, e.g., during sexual activity, have reduced osmolality as compared to prior art single-phase lubricants containing glycols, and are advantageously less costly than conventional silicone based lubricants, while being clear, translucent, hand-clear, or substantially clear or translucent.

A current method employed to slow the separation of the silicone and water phases is to add a sufficient amount of a viscosity modifier (thickener) to obtain the desired shelf stability. For this reason, silicone-containing emulsion lubricants may commonly have viscosities greater than 20,000 cps. As noted previously, such high viscosity lubricants are generally not well accepted by the public, e.g., are generally not easily useable, in intimate care applications. For example, thick jellies are not considered as easy and convenient to use as liquids.

Each and every patent, patent publication, and non-patent publication cited or mentioned in this patent application is hereby incorporated by reference herein in its entirety.

In accordance with the present invention, new lubricant compositions useful in intimate care applications, condom products packaged with such lubricants, and methods of making and using such new intimate care lubricant compositions, have been discovered. In one aspect of the invention, substantially clear or translucent, stable, low viscosity silicone-in-water emulsions have been discovered which are excellently suited for use as lubricants in one or more intimate care applications, for example, as a personal lubricant involving one or more body parts, for example, private body parts, on which such a composition, is placed and/or used during sexual activity. In other applications, the stable low viscosity silicone-in-water emulsions of the present invention may be used as a surgical lubricant or as a skin treatment to prevent skin damage due to chafing. In still other applications the compositions of the present invention may be useful as vehicles for one or more pharmaceutically active agent.

Preferred silicone-in-water lubricating emulsions contain one or more silicone lubricants and a water-containing hydrophilic phase. Among the silicone lubricants that may be included in these compositions are, without limitation, one or more of dimethicone fluids, dimethicone gums, dimethiconol fluids, dimethiconol gums, silicone crosspolymers and elastomers, ethoxylated dimethicone fluids, phenyl silicones, alkyl silicones, alkyl silanes, and the like; and combinations thereof. It will be clear to the person of ordinary skill that otherwise identical substituted and unsubstituted dimethicones and dimethiconols are generally interchangeable ingredients in the lubricant compositions of the present invention.

The present substantially clear or translucent, stable, silicone-in-water emulsions lubricants can be produced using silicone lubricant(s), for example, a silicone lubricant as noted above, in combination with one or more (for example, two or more) non-ionic surfactants. Such surfactants may comprise, without limitation, ethoxylated fatty alcohol surfactant emulsifiers. These ingredients are preferably mixed to create a water-in-silicone emulsion, then the emulsion is inverted to a silicone-in-water emulsion using phase inversion processing techniques to reduce the droplet/particle size of the emulsion's silicone phase, thereby reducing viscosity as desired.

In the present invention, the average diameter of the aqueous phase-dispersed silicone droplets is less than about 1 micrometers (μm) and greater than about 99 nm; such as less than 999 nm, or less than about 600 nm, or less than about 500 nm, or less than about 400 nm, and greater than 99 nm. In preferred examples the droplet size is between about 200 nm and about 400 nm, or about 300 nm.

Applicants have found that average droplet sizes in this range cause a reduction in the viscosity of the emulsion as compared to otherwise identical emulsions having a larger average droplet size, while at the same time requiring less surfactant and/or rheology modifier to form a stable emulsion than is the case in a microemulsion, in which the average droplet size is less than about 99 nm. Lower surfactant concentration is desirable for greater comfort and results in a lower overall osmolality.

The viscosity of the lubricant products obtained in accordance with this invention may be further controlled to the desired viscosity by the addition of water-miscible rheology modifiers. Such agents may, without limitation, include one or more of the following: alginates, carboxymethyl cellulose, dextrins, modified starches, xanthan gums, guar gums, hydroxypropyl guar, hydroxyethyl cellulose, xanthan gums, carbomers, polyacrylic acid, cellulose and cellulosic derivatives (such as, without limitation, hydroxyethyl cellulose or carboxymethyl cellulose), polycarbophil, gelatins, dextrin, polysaccharides, polyacrylamide, polyvinyl alcohol, polyvinyl acetate, polyvinyl pyrrolidone (PVP) and derivatives thereof and/or mixtures thereof.]

In another aspect of the present invention, it has been discovered that clear, hand-clear, or substantially clear, stable, low viscosity silicone-in-water lubricant emulsions containing one or more silicone lubricants including, but not limited to, dimethicone fluids, dimethicone gums, dimethiconol fluids, dimethiconol gums, silicone crosspolymers and elastomers, ethoxylated dimethicone fluids, phenyl silicones, alkyl silicones, alkyl silanes and combinations thereof, can be effectively, for example, easily and/or economically, produced and used as lubricants in intimate care applications. By "hand-clear" is meant that when the product is applied to the hand, the product appears clear or substantially clear on the skin.

In another aspect of the invention, methods of making clear or substantially clear, hand-clear, stable, low viscosity silicone-in-water lubricant emulsions are provided. Such methods may include combining one or more silicone lubricants including but not limited to dimethicone fluids, dimethicone gums, dimethiconol fluids, dimethiconol gums, silicone crosspolymers and elastomers, ethoxylated dimethicone fluids, phenyl silicones, alkyl silicones, alkyl silanes, and combinations thereof, together with one or more, for example, two or more, non-ionic surfactant, and employing a phase inversion processing technique to reduce the droplet/particle size of the silicone phase as desired, for example, to a size less than about 999 nanometers and greater than about 99 nm. Preferably the average droplet size is between about 100 nm and about 800 nm, or between about 150 nm and about 600 nm; or between about 200 nm and about 400 nm; and more preferably about 300 nm (plus or minus 50 nm). In currently preferred examples of the invention, one or more non-ionic surfactant may comprise an ethoxylated fatty alcohol.

In one example, a lubricant composition of the present invention may comprise water, a silicone lubricant, for example, about 15% to about 40% by weight of a silicone lubricant; about 15% to about 40% by weight of a water-miscible glycol component, preferably in an amount to cause the aqueous phase to have a refractive index that substantially matches the refractive index of the silicone phase; and at least one or a combination of two or more non-ionic surfactants.

Preferably, refractive index matching may be achieved by adjusting the refractive index of the aqueous phase of the emulsion, in conjunction with causing phase inversion of the emulsion. Phase inversion processing techniques may be employed in the manufacture of the compositions of the present invention. In a preferred method, for example, a small amount of water or aqueous phase (see below; about 5% wt to about 20% wt, or about 10% wt of the mass of the total final formulation) is added to the silicone phase containing the silicone lubricant, the nonionic surfactants and a rheology modifier. Mixing the resulting combination to a uniform "thick phase" at moderate agitation for a period of time results in the formation of a water-in-silicone emulsion.

The aqueous phase is made up in a separate vessel using water and a sufficient amount of glycol to at least approximately match the refractive index of the silicone phase in the final formulation.

The aqueous phase is then added slowly with gentle mixing to the silicone phase. This converts the water-in silicone emulsion into a silicone-in-water emulsion, for example, an emulsion in which the average droplet size of the silicone phase particles or droplets is reduced to between about 99 nm and about 999 nanometers, or between about 100 nm and about 800 nm, or between about 150 nm and about 600 nm; or between about 200 nm and about 400 nm; or about 300 nm. In currently preferred examples of the invention, one or more non-ionic surfactant may comprise an ethoxylated fatty alcohol.

Following phase inversion it may sometimes be necessary to titrate a small amount of one or more RIAA, e.g., small, additive amounts of water (to lower the RI)) or a glycol such as PEG-12 (to raise the RI) into the product to obtain good clarity by matching the refractive indices of the silicone phase and the aqueous phase in the final product. In other, currently less preferred embodiments the RIAA may be miscible with the silicone phase and immiscible with the aqueous phase, thereby adjusting the RI of the silicone phase.

The phase-inverted silicone-in-water emulsion is clear or translucent (or substantially clear, or hand-clear) and very appealing to the eye. By "substantially clear or translucent" is meant that the composition appears homogeneous, lacks visible precipitated solids, and is not opaque or cloudy.

The refractive index (n) is a dimensionless term specific for a given medium comprising a ratio of the speed of light in a vacuum (c) and the speed of light through the medium at issue (v). Thus, the refractive index of a medium is expressed as n=c/v according to Snell's law. The refractive index is conventionally determined at 25° C. The refractive index of water is 1.3330, while, for example, the refractive index of a preparation of cyclomethicone, phenyltrimethicone and dimethicone (sold as Gelaid™ 5565 by Chemsil Silicones, Inc.) is 1.4015.

If the refractive indices of two clear immiscible flowable phases are made to equal each other, then the angle of refraction of light through the media will also be equal, and an emulsion made from each of these separately clear compositions will also be clear.

If several miscible fluid phases are mixed together to form a clear, homogeneous flowable phase, the refractive indices of each such ingredient can be used to calculate the refractive index of the final phase. See e.g. Sun et al., J. Cosmet. Sci. 56, 253-265 (July/August 2005). Usually (but not always) the calculated value of the mixture's refractive index ("RI") will agree with the experimentally determined value quite closely. When the determined value of RI is significantly different to the calculated or desired RI, some adjustment may be necessary. Such blending and adjustment to achieve a desired RI is within the capability of those skilled in the art.

Thus, it is possible to separately mix ingredients of each of two immiscible clear phases (for example, aqueous phase-miscible ingredients and silicone miscible ingredients) so that each phase has a substantially equal RI to the other phase. In such case, upon combining the phases the resulting mixture or emulsion is clear or translucent.

By "matched" or "identical" refractive indices is meant that the difference between the refractive indices (RIs) of the matching, immiscible fluid phases is no more than about 0.0005 RI unit. All RIs mentioned herein refer to refractive indices measured at room temperature (23° C.). Preferably, the respective refractive indices of the silicone and hydrophilic components of the composition are made to match within about 0.0001 unit, or within about 0.0002 units, or within about 0.0003 units, or within about 0.0004 units or within about 0.0005 units. By "substantially matching" or substantially identical" refractive indices is meant within about 0.001 units, or within about 0.005 units, or within about 0.01 units. Particularly preferably, the difference between the RIs is no more than about 0.0002 unit.

Alternatively, the refractive indices of the immiscible components of the composition are made to match within about 1% or about 2% or within about 4% or within about 8% or within about 10% or within about 15% or within about 20% of each other. In another alternative embodiment, the refractive indices of the immiscible components of the composition are made to match sufficiently so as to render substantially undetectable an interface between the phases under ordinary lighting, so as to render the composition substantially uniform and clear or translucent.

By "high refractive index" is meant having a refractive index greater than that of water (1.3330).

The compositions of the invention may, in certain examples, be used as vehicles for one or more pharmaceutically or cosmetically active agent. Such active agents may include, for example, and without limitation, humectants, moisturizers, anti-oxidants, pigments, dyes, anti-fungal agents, chelating agents, antimicrobial agents, analgesics, preservatives, and skin conditioning agents and one or more other suitable components, as desired.

The present low viscosity silicone-in-water emulsions are stable and clear, substantially clear, hand-clear or translucent, non-irritating to skin, and are useful in or as lubricants, for example, in lubricants for intimate care applications, either alone, or in association with condom products. Additionally, the compositions of the present invention may be used as surgical lubricants or as a skin-care treatment.

These and other aspects and advantages of the present invention will become apparent when considered in light of the following detailed description and claims.

DETAILED DESCRIPTION

The present invention is drawn to new stable, substantially clear or translucent, low viscosity multi-phasic lubricant compositions, including, but not limited to, new lubricants useful in intimate care applications, and to new methods of making such lubricants.

In another example, the present lubricant compositions comprise at least two substantially immiscible phases comprising:
 a) an aqueous phase;
 b) a silicone fluid component;
 c) at least one non-ionic surfactant component, preferably at least two different non-ionic surfactant components;
 d) at least one rheology modifier component; and
 e) optionally, at least one RIAA component. Preferably, an RIAA component is a water-miscible component, such as a glycol component.

In another example, the silicone-in-water emulsion composition may comprise: purified water at a sufficient quantity to add up to 100% by weight when combined with the other components; from about 20% to about 40% by weight of a high refractive index glycol or a combination of two or more high refractive index glycols, for example, in a sufficient quantity when mixed into the aqueous phase to cause the refractive index of the aqueous phase to match or substantially match the refractive index of the silicone lubricant; from about 1% to about 6% by weight of one or more non-ionic surfactants; from about 0.1% to about 0.8% of one or more polymeric emulsifier; and from about 15% to about 60% by weight of a silicone lubricant or combination of silicone lubricants. In currently preferred examples of the invention, one or more non-ionic surfactant may comprise an ethoxylated fatty alcohol.

The present lubricant compositions are very preferably substantially or completely clear or hand-clear or transparent. Preferably, the respective refractive indices of the silicone phase and hydrophilic phase of the present compositions are made to be at least substantially identical.

In another embodiment, the refractive indices of the immiscible phases of the composition are made to match sufficiently so as to render substantially undetectable an interface between the phases under ordinary lighting, at room temperature, or so as to render the composition substantially clear or translucent.

In preferred embodiments the lubricant composition is effective as a lubricant having a lubricity greater than that of water, is useful in intimate care applications, and is, substantially non-irritating to body parts, for example, private body parts of an animal or human such as, for example, skin and oral, anal, penile, and vaginal mucosa and the like, particularly during sexual activity.

In preferred embodiments the lubricant component is washable from cotton fabric without staining, in warm water in a washing machine under a normal washing cycle, as distinct from silicone-based single phase lubricants, which displays staining of cotton fabric under identical washing conditions.

The stability of the stable, low viscosity silicone-in-water lubricant emulsions in accordance with the present invention may be at least partially controlled or affected by the nature and/or amount of the thickener(s)/rheology modifier(s) employed, and the amount and rate of addition of water initially added to the silicone phase with slow mixing in order to create a thick or viscous water-in-silicone emulsion paste. Advantageously, only enough agitation is used to provide a substantially uniform thick phase. This thick phase is gently mixed for a period of time until uniform. This is followed by the slow addition of the remaining aqueous phase at higher agitation for sufficient time to cause a phase inversion of the emulsion from a water-in-silicone emulsion to a silicone-in-water emulsion. The final silicone-in water emulsion preferably has, for example, an average droplet/particle size less than about 999 nanometers and greater than about 99 nm. Preferably the average droplet size is between about 100 nm and about 800 nm, or between about 150 nm and about 600 nm; or between about 200 nm and about 400 nm; and more preferably about 300 nm (plus or minus 50 nm).

Very preferably, an effective amount of a high refractive index glycol component is added as a component of the stable, low viscosity, silicone-in-water emulsion lubricant in order to raise the RI of the aqueous phase to substantially match that of the silicone phase, resulting in a RI-matched lubricant composition which is substantially clear or translucent and effective for use as a personal lubricant in one or more intimate care applications. An RIAA is used in small amounts effective to cause the refractive index of the water phase to substantially match that of the silicone lubricant phase. Also, preferably the RIAA(s) are water-miscible.

"Stability" means the ability of an emulsion, once formed, to resist changes in its physiochemical properties with time.

Such changes may include changes over a given time in color, clarity, odor and separation (e.g., creaming, settling, and/or precipitant formation) A stable emulsion also displays no significant measurable change in other product specifications such as pH, viscosity, performance, and other measurable product specifications.

It is generally accepted in the art that incubation of a given emulsion formulation for 8 weeks at 45° C. can be equated to incubation of the same product for 1 year at room temperature. Stability testing is conducted using aliquots of the same product contained in both a glass container and in the packaging used to deliver the product in commerce. Such testing can help rule out interactions between the packaging materials and the product itself as a causal factor in emulsion instability. Stability testing is advantageously carried out by a person skilled in the art with respect to the specific combination of ingredients used in the formulation, so that the stability testing may be modified to adequately test the stability of the formulation under various storage, shipping and on-shelf environment conditions.

Additionally, a prospective emulsion product should undergo freeze-thaw stability testing to determine what happens if the product freezes in storage or transportation. A product sample may be frozen overnight and thawed the next day to determine if any of the product specifications has changed. This is typically done for 3 to 5 cycles before a conclusion that the product is stable is confidently reached.

The resulting product is a stable, low viscosity, clear, hand-clear, or substantially clear, silicone-in-water emulsion lubricant having high lubricity and useful in intimate care applications.

The present lubricants may be used as sexual lubricants, or may be useful in one or more other applications; for example, as a surgical lubricant, skin smoothener, friction-reducing skin treatment, makeup foundation and the like.

The viscosity of the compositions of the present invention may be adjusted as desired. For example, the viscosity may be altered, at least in part, by increasing or decreasing the amount of the silicone phase or the molecular weight(s) and/or concentration(s) of one or more rheology modifiers used.

Examples of alkylene glycols and their derivatives that can be used to act as RI adjusting additives to adjust the RI values of a hydrophilic phase in the present compositions. Water-miscible RI adjusting additives may include, without limitation, propylene glycol, butylene glycol, hexylene glycol, glycerin and glycereth-7. Additionally, polyalkylene glycols, for example, PEG-4 (having an average of 4 ethylene oxide units), PEG-6 (having an average of 6 ethylene oxide units), PEG-8 (having an average of 8 ethylene oxide units), PEG-12 (having an average of 12 ethylene oxide units, PEG 200 (polyethylene glycol with an average molecular weight of 200 Daltons), PEG 400 (with an average molecular weight of 400 Daltons), PEG 600 (polyethylene glycol with an average molecular weight of 600 Daltons), PEG-7M (having an average molecular weight of about 7000), PEG 14M (having an average molecular weight of about 14000), PEG-20M (having an average molecular weight of about 20000), PEG-45M (having an average molecular weight of about 45000) and PEG-90M (having an average molecular weight of about 90000), and mixtures of two or more thereof may be used to fine-tune the RI values of the aqueous phase.

Furthermore, those of ordinary skill in the art are aware that certain water-miscible RIAAs may have an effect upon the refractive index of the aqueous phase that is greater than or less than the calculated value for that RIAA obtained using Equation 1 or 2 shown above. Such an effect is referred to as a "deviation" from the expected RI.

In systems having an aqueous component, when aqueous concentration is plotted against RI the largest deviation from calculated RI values among selected alkylene glycols are seen using hexylene glycol (which deviates upward from the calculated RI value). Other glycols, such as propylene glycol, butylene glycol, hexylene glycol, and polyethylene glycol also show positive deviation from the calculated values.

Because osmolality of the aqueous phase of an emulsion is a colligative property (depending on the ratio of the number of solute particles to the number of solvent molecules in a solution, and not on the nature of the chemical species present), one of ordinary skill in the art wishing to minimize osmolality may select an RIAA having a high MW as well as a suitable RI. Selection of an RIAA to optimize RI and osmolality is within the capability of those skilled in the art.

The present compositions will often, but not invariably, contain a preservative component. Such a component will comprise any suitable and effective preservative that is generally regarded as safe and non-irritating when applied to the skin. The compositions of the present invention preferably contain preservative components such as Glydant Plus® (DMDM hydantoin (1,3-bis(hydroxymethyl)-5,5-dimethylimidazolidine-2,4-dione) and iodopropynyl butylcarbamate) or any other cosmetically or pharmaceutically safe and effective preservative component. For example, and without limitation, other preservative components may comprise methylparaben, benzoic acid, sorbic acid, gallic acid, propylparaben and the like and mixtures thereof. The preservative component may be present, if at all, in the present compositions in an amount in a range of about 0.01% or less to about 0.5% or more by weight, depending on the specific preservative activity of the preservative. In certain embodiments, a preservative may be chosen to be soluble in one of the immiscible phases. In certain embodiments, a preservative may be chosen to be soluble in each of the immiscible phases. In other embodiments, more than one preservative may be used, preferably with at least one preservative soluble in two or more, or each, of the immiscible phases of the composition.

Additionally the present compositions comprise a hydrophilic phase. The hydrophilic phase usually and preferably contains a water-miscible polymer; e.g., a rheology modifier, such as, without limitation, an acrylate component. In certain embodiments the hydrophilic phase may comprise water; in other embodiments it may be substantially anhydrous. In some embodiments of the compositions of the invention the rheology modifier may include one or more of the following components: a polyacrylamide component, an acrylates/C10-30 alkyl acrylate crosspolymer, a carbomer, a natural gum, an acrylamide/sodium acryloyl dimethyl taurate copolymer component, a hydroxyethyl acrylate/sodium acryloyl dimethyl taurate copolymer component, a polyacrylate-X component, and/or a sodium acrylate/sodium acryloyl dimethyl taurate copolymer component.

In certain aspects of the invention fragrances, colors, and/or flavors may be added to the lubricant compositions of the present invention to enhance the subjects' pleasure when using the lubricant. For example, such fragrances may include, without limitation, a citrus (e.g., orange, lime, grapefruit), a melon (e.g., watermelon or honeydew), a berry fragrance, frankincense, myrrh, mango, coconut, vanilla, cucumber, patchouli, and the like.

Similarly, the lubricant may be made using a flavor, for example (if a fragrance is also used) a corresponding flavor, such as, without limitation, a citrus (e.g., orange, lemon, lime, grapefruit), a melon (e.g., watermelon or honeydew), a berry, other fruits or spices (such as mango, coconut, vanilla), and the like. Sweeteners may also be used, such as sugars, saccharin, aspartame, sucralose, neotame, and acesulfame potassium.

Similarly, the lubricant may be made using a physiological cooling agent, such as, for example, menthol and derivatives thereof (e.g., peppermint oil), stearyl neopentanoate, eucalyptus oil, camphor, and the like.

Notwithstanding the above, in other embodiments the invention of the present application may be made to be odorless and/or tasteless. An unflavored or unscented lubricant is not only favored by many people, but may tend to be less allergenic or irritating to these having sensitive skin.

The compositions of the present invention may also be useful as massage liquids, gels and creams. Due to the presence of silicone component(s), the lubricant composition may be useful as a skin conditioner.

In preferred examples, the compositions of the present invention lack suspended solids, such as insoluble solid particulate material, solid fractal particles such as metal oxides, gels made using such solid particles, and the like. Such insoluble particulate materials may cause increased friction and irritation of skin tissues, particularly sensitive skin tissues, and compositions containing such are defined herein as being definitionally excluded from the scope of the term "suitable for use as a lubricant in one or more intimate care applications", or similar terminology used herein.

Certain of the compositions of this invention may be manufactured and used as personal lubricants that convey a feeling of warmth. For example, and without limitation, emulsions that lack water, or in which the hydrophilic component contains about 10 wt % water or less, can be made according to the present invention using a hydrophilic component comprising one or more hydrophilic compound that is exothermic when diluted with water; for example, a glycol or mixture of glycols. The feeling of warmth generated by such compositions is soothing and/or stimulating to the skin or mucous membranes where they are applied. The compositions of this embodiment of the invention may convey a feeling of warmth when applied, for example, to vaginal, anal, or oral mucosa. Such warming effect has been found to enhance intimacy and increase pleasure during sexual activities.

In addition to their use as lubricants per se, the present compositions may be used to relieve vaginal dryness or dry mouth, to moisturize skin, to provide an ameliorating effect for frostbite or extremities overexposed to the cold and the like applications. The present compositions may be useful for treating conditions of infection on the skin or mucosa while soothing the area of infection.

In certain circumstances the present compositions may also be used as vehicles to deliver a pharmaceutically active agent or other treatment agents to skin, for example, biomembranes. Such agents may include, but are not limited to, hormones, antimicrobials, antibacterials, antibiotics, non-steroidal anti-inflammatory agents, spermicides, immunodilators, anaesthetics, plant extracts, vitamins, corticosteroids or antifungal agents and the like and mixtures thereof.

Antifungal agents are preferably azoles or imidazoles, including by not limited to, miconazole, econazole, terconazole, saperconazole, itraconazole, butaconazole, clotrimazole, tioconazole, fluconazole and ketocanazole, vericonazole, fenticonazole, sertaconazole, posaconazole, bifonazole, oxiconazole, sulconazole, elubio, vorconazole, isoconazole, flutimazole, tioconazole and their pharmaceutically acceptable salts and the like. Other antifungal agents may include an allylamine or one from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

The present compositions, for example, for vulvovaginal or other mucosal use, may include one or more antibiotics including, but not limited to, metronidazole, clindamycin, tinidazole, ornidazole, secnidazole, refaximin, trospectomycin, purpuromycin and their pharmaceutically acceptable salts and the like and mixtures thereof.

The present compositions, for example, for vulvovaginal or other mucosal use, may include one or more antiviral agents including but not limited to, immunomodulators, such as imiquimod, derivatives thereof, acyclovir, valacyclovir, famicyclovir, podofilox, podophyllin, interferon alpha, cidofovir, nonoxynol-9, pharmaceutically acceptable salts thereof and the like and mixtures thereof.

The present compositions may include one or more spermicides including, but not limited to, nonoxynol-9, octoxynol-9, dodecaethyleneglycol monolaurate, laureth 10S, and methoxypolyoxyethyleneglycol 550 laurate and mixtures thereof.

The present compositions may include antimicrobial agents, including but not limited to, chlorohexidine gluconate, sodium polystyrene sulfonate, sodium cellulose sulfate, silver particles of micro- and sub-micrometer sizes, silver salts and other antibacterial agents known to the art and the like and mixtures thereof.

The present compositions may include local anesthetics, including but are not limited to, benzocaine, lidocaine, dibucaine, benzyl alcohol, camphor, resorcinol, menthol and diphenylhydramine hydrochloride and the like and mixtures thereof.

The present compositions may include plant extracts such as aloe, witch hazel, chamomile, hydrogentated soy oil and colloidal oatmeal, vitamins such as vitamin A, D or E, CBD oil (hemp oil), corticosteroids such as hydrocortisone acetate, stearol esters, and the like and mixtures thereof.

The present compositions, for example, for vulvovaginal or other mucosal use, may include one or more hormones for treating a decrease in estrogen secretion in the woman in need of estrogen replacement, such as women with vaginal atrophy. The hormones may include, but are not limited to, estrogen elected from the group consisting of estradiol, estradiol benzoate, estradiol cypionate, estradiol dipropinonate, estradiol enanthate, conjugated estrogen, estriol, estrone, estrone sulfate, ethinyl estradiol, estrofurate, quinestrol and mestranol and the like and mixtures thereof.

The present compositions may contain agents known to those of skill in the art to treat female sexual dysfunction (including treating one or more different aspects of female sexual dysfunction such as female sexual arousal disorder, hypoactive sexual desire disorder, orgasmic disorder and the like) as well as those that treat dyspareunia and/or vaginismus or vulvodynia and to relieve pain upon intercourse. Such agents include drugs such as sildenafil, tadalafil, vardenafil, and flibanserin; natural or synthetic hormones such as tibolone (7α-methylnoretynodrel), prostaglandin, and testosterone; calcium channel blockers; cholinergic modulators, phosphodiesterase inhibitors; alpha-adrenergic receptor antagonist; beta-adrenergic receptor agonists; cAMP-dependent protein kinase activators; superoxide scavengers; potassium channel activators; estrogen-like compounds; testosterone-like compounds; benzodiazepines; adrenergic nerve inhibitors; HMG-COA reductase inhibitors; smooth muscle relaxants; adenosine receptor modulators and adenylyl cyclase activators. Additionally, or alternatively, the present compositions may contain vasodilators such as methyl nicotinate, histamine hydrochloride and very small non-irritating amounts of methyl salicylate.

The present compositions, for example, for vulvovaginal use, may contain one or more analgesics and/or nonsteroidal anti-inflammatory agents for treating dysmenorrhea or menstrual cramping. The analgesics and nonsteroidal anti-inflammatory agents may include, but are not limited to, aspirin, ibuprofen, indomethacin, phenylbutazone, bromfenac, fenamate, sulidac, nabumetone, ketorolac, and naproxen and the like and mixtures thereof.

It will be understood that the present compositions may contain one or more agent falling within two or more of the functional categories indicated above, or a plurality of agents which, in combination, falls within more than one of these functional categories.

While this invention is being described with respect to various specific examples and embodiments, it is to be understood that the invention is not limited to these examples and embodiments, and is defined solely by the claims and that it can be variously practiced within the scope of the following claims.

EXAMPLES

Components used in the examples include ingredients having the following trade names or abbreviations:
CRL-3032 is a blend of dimethicone (and) cyclopentasiloxane (and) cyclohexasiloxane.
CF 3557-OH is a blend of dimethicone (and) cyclopentasiloxane (and) dimethiconol (and) phenyltrimethicone.
CF 0515-OH is a blend of dimethicone (and) dimethiconol.
CF 2002-DM is a blend of dimethicones of different viscosities.
CF 7007-OH is a blend of dimethicone (and) dimethicone/vinyl dimethicone crosspolymer.
EMT-10 is hydroxyethyl acrylate/sodium acryloyl dimethyl taurate.
Laureth-4 is polyoxyethylene glyol (4) lauryl ether.
Laureth-24 is polyoxyethylene glyol (24) lauryl ether.
Deceth-5 is polyoxyethylene glyol (5) decyl ether.
Ceteareth-25 is polyoxyethylene (25) cetyl/stearyl ether.
PEG 90M is a polymer of ethylene glycol (i.e. polyethylene glycol) having an average of 90,000 units of ethylene glycol.
PEG 8 is a polymer of ethylene glycol having an average of 8 units of ethylene glycol.
PEG 4 is a polymer of ethylene glycol having an average of 4 units of ethylene glycol.
C12-13 Pareth-3 is a polyethylene glycol ether of a mixture of synthetic $C_{12-13}$ fatty alcohols with an average of 3 moles of ethylene oxide.
C12-13 Pareth-23 is a polyethylene glycol ether of a mixture of synthetic $C_{12-13}$ fatty alcohols with an average of 23 moles of ethylene oxide.

In the examples of the invention presently shown the RIAA is a water-miscible component, preferably a fluid, added to the final silicone-in-water emulsions composition to raise or lower the RI of the aqueous phase to substantially match the RI of the silicone phase.

However, those of ordinary skill in the art will be aware that in other, currently less preferred examples (not shown here) the RIAA may be miscible with the silicone phase, preferably a fluid, which is added to the silicone-in-water composition to raise or lower the RI of the silicone phase to substantially match the RI of the aqueous phase.

Hence Applicants hereby describe herein silicone-in-water compositions using only one or more water-miscible ingredients as an RIAA(s). In these compositions the RIAA(s) are very preferably, immiscible with the silicone phase. In other examples the compositions of the invention are drawn to silicone-in-water compositions using only one or more silicone miscible ingredients as an RIAA(s); in these compositions the RIAA(s) are very preferably immiscible with the water phase. In still other examples the compositions of the invention are drawn to silicone-in-water compositions using both water-miscible and silicone-miscible RIAAs.

The non-exclusive list below shows some compounds which may be titrated into the composition as RIAAs, with mixing, once the phase inversion from a water-in-silicone emulsion to a silicone in water emulsion has occurred.

| Ingredient | Ri | Miscibility |
|---|---|---|
| Water, Deionized | 1.3330 | Aqueous |
| Glycerin | 1.4680 | Aqueous |
| Hexylene glycol | 1.4276 | Aqueous |
| Butylene glycol | 1.4401 | Aqueous |
| Propylene glycol | 1.4355 | Aqueous |
| Glycereth-7 (Liponic EG-7, Lipo Chemicals) | 1.4720 | Aqueous |
| Glycereth-26 (Liponic EG-1, Lipo Chemicals) | 1.4690 | Aqueous |
| PEG-4 (Carbowax PEG 200, Union Carbide) | 1.4582 | Aqueous |
| PEG-6 (Carbowax PEG 300, Union Carbide) | 1.4615 | Aqueous |
| PPG-9 (Polyglycol P-425, Dow Chemical) | 1.4455 | Aqueous |
| PVP/VA copolymer (Luviskol VA 73W, BASF AG) | 1.4275 | Aqueous |
| PVP (Luviskol K30, BASF AG) | 1.3805 | Aqueous |
| Cyclomethicone and dimethicone (DC 1501, Dow Corning) | 1.3972 | Silicone |
| Cyclomethicone (Rhodorsil 45V5, Rhodia) | 1.3960 | Silicone |
| Cyclomethicone, phenyltrimethicone, and dimethicone (Gelaid 5565, Chemsil) | 1.4015 | Silicone |
| Cylomethicone and dimethicone copolyol (DC 5225, Dow Corning) | 1.3975 | Silicone |
| Polyacrylamide, C13-14 isoparaffin, and laureth-7 (Sepigel 305, Seppic) | 1.4460 | Silicone |
| Sodium acrylate/acryloyldimethyl taurate copolymer, isohexadecane, and polysorbate 80 (Simugel EG, Seppic) | 1.4450 | Aqueous |
| Hydroxyethylacrylate/sodium acryloyldimethyl taurate copolymer, squalene, and polysorbate 60 (Simugel NS, Seppic) | 1.4475 | Aqueous |
| C13-14 isoparaffin (Isopar M, Exxon Mobil Chemical) | 1.4380 | Silicone |
| C11-13 isoparaffin (Isopar L, Exxon Mobil Chemical) | 1.4255 | Silicone |

Example 1

The following examples are provided in order to more fully illustrate various examples of the invention, which is not limited to embodiments shown in these examples. Unless otherwise indicated, all parts and percentages are by weight.

In Example 1 the percentages of each ingredient in each of three (3) components of the composition, identified as Component A, Component B and Component C together total 100% of the final composition. Small amounts of a fourth component, which may be termed Component D, consists of a water-miscible RIAA, in this example selected from the group consisting of water to lower the RI of the aqueous phase, and a glycol (such as an alkylene glycol), to raise the RI of the aqueous phase.

The following ingredients were combined as discussed below.

TABLE 1

| Component A | |
|---|---|
| CRL-3932 silicone lubricant | 30 wt. % |
| Thickening polymeric hydrophilic rheology modifier (hydroxyethyl acrylate/sodium acryloyl dimethyl taurate, sold by SEPPIC under the trade name Sepinov ™ EMT 10) | 0.4 wt. % |
| ethoxylated fatty alcohol surfactant emulsifier (polyoxyethylene (4) lauryl ether, sold as Laureth-4) | 2.0 wt % |
| ethoxylated fatty alcohol surfactant emulsifier (polyoxyethylene (23) lauryl ether, sold as Laureth-23) | 2.0 wt % |
| Component B | |
| Water | 10.0 wt % |
| Component C | |
| Water | 27.6 wt % |
| PEG 45M (polyethylene glycol having an average of 45,000 ethylene glycol units) | 0.1 wt % |
| PEG-12 polyethylene glycol having an average of 12 ethylene glycol units | 27.9 wt % |

For Example 1, the anhydrous silicone lubricant component and the non-ionic surfactant emulsifiers are measured into a suitable vessel equipped for heating and sized to hold the entire final batch of product. The silicone lubricant component if solid, is heated at a temperature at least equal to the melting point of the silicone lubricant component having the highest melting point to form a uniform silicone phase. The thickening rheology modifier (e.g., hydroxyethyl acrylate/sodium acryloyl dimethyl taurate) is added to the silicone lubricant paste, and mixed at 45°–50° C. (a temperature at least equal to the melting point of the component having the highest melting point) to melt the components sufficiently to permit them to form a uniform hydrophobic silicone phase. In some cases, depending upon the nature of the rheology modifier (for example, whether it is an emulsifying thickener or not), the rheology modifier may be added to Component C (see Table 1 and below) rather than to the hydrophobic silicone phase.

About 10% (by weight of the total amount of the final formulation) of Component B (water) is slowly added to the silicone phase and gently mixed until a thick, uniform water-in-silicone emulsion is obtained. In this example, the batch is gently mixed to uniformly blend the ingredients together (e.g., from between about 30 or about 40 minutes to about 70 or 80 minutes. Care should be taken to employ limited agitation, for example, only enough or significant agitation to mix the ingredients uniformly. For example, such mixing can be done with side sweep agitator or preferably a combination of low shear mixing blade (propeller) with a side sweep agitator.

In general, the amount of water and mixing time is determined by experimentation; in this example and many other formulations having relatively high silicone content, the slow addition of about 10% by weight of water with mixing results in a final formulation with the desired average particle size of about 300 nm. However, this amount of water may vary from about 5% to about 20% by weight of the total amount of the final formulation depending upon the nature and amounts of the ingredients (e.g., rheology modifier(s), silicone lubricant(s), non-ionic surfactant(s) and the like).

Preferably the mixing time is between about 30 or about 40 minutes to about 70 or 80 minutes, but in some cases may exceed this range.

In some cases, depending upon the specific formulation and ingredients, it may be desirable to use a portion (about 5% to about 20% by weight of the total amount of the final formulation) of the aqueous phase to add to the silicone phase in forming the water-in-silicone emulsion, rather than water alone.

There is, or appears to be, a relationship between the amount of water introduced into the Component A nonionic emulsifier combination, the critical micelle concentration (the concentration of a surfactant above which micelles form and all additional surfactants added to the system are incorporated in micelles; "CMC"), and the mixing time required to obtain the optimal or desired droplet size. Thus, for a given formulation it may be desirable to conduct two or more experiments, e.g., a series of experiments, to determine the most effective conditions (parameters, e.g. amount of water, rate of water addition, CMC and mixing time) to obtain the right or desired droplet size: preferably between about 200 nm and about 500 nm, or the right or desired range and/or distribution of droplet sizes.

In a separate container the water and the PEG-45M of Component C are mixed and thoroughly dissolved. Then the PEG-12 of Component C is added, and the Component C ingredients are mixed until uniform.

In Example, 1, when the water-in-silicone emulsion is mixed for about 1 hour, the combined, mixed Component C is slowly added with moderate agitation for a sufficient time period to fully mix the ingredients, to provide rapid turnover of the batch, and cause phase inversion of the water-in-silicone to a silicone-in-water emulsion. High shear during mixing is to be avoided; Applicants have found that high shear will actually increase the droplet size of the emulsion. The mixing time may require empirical determination to result in a uniform emulsion in which all the silicone phase is completely dispersed in the water phase.

While quite important, obtaining an optimal average particle size of about 300 μm is not always critical to achieving a stable emulsion; adding more of the rheology modifier may also help stabilize the composition of the present invention if the optimal average particle size (e.g., about 300 nm) has not been precisely achieved, or if the particle size distribution is not optimally narrow.

Since the present emulsion products are clear, hand-clear or translucent emulsions, or substantially clear and translucent emulsions, it may be necessary to titrate small, stepwise amounts of a aqueous phase-miscible RIAA, e.g., water (to lower the RI of the aqueous phase) or a glycol (e.g. PEG-12; to raise the RI of the aqueous phase) into the final emulsion to improve clarity by further matching the refractive indices of the silicone phase and the aqueous phase in the final product.

The final product, produced as noted above, is a clear silicone-in water emulsion which is capable of desirable low viscosity, high stability, and is effective and safe when used as a lubricant in intimate care applications.

A general method of making a product in accordance with the present invention is as follows.
1) Add one or more silicone lubricant to a vessel large enough to hold the final formulation volume.
2) Add the non-ionic surfactant emulsifier(s) to the silicone lubricant and heat, if necessary—some non-ionic surfactant emulsifiers may be solid; for example, waxy solids, at room temperature. All ingredients should be in a flowable form. The ingredients' temperature should be at or above the melting point of the non-ionic surfactant having the highest melting point.

3) Add the rheology modifier, either to the silicone/non-ionic surfactant mixture, or into the water/glycol phase described in step 4. This is determined based on the characteristics of the specific formulation and of the rheology modifier to be used. Such characteristics may include the following considerations.

Some rheology modifiers are supplied in water and may therefore be suitable for addition to the aqueous phase. Other rheology modifiers are not readily dispersible in the silicone phase, and therefore must be added to the aqueous phase. If a particular formulation uses a small amount of water in Component C addition of a rheology modifier to the aqueous phase may be difficult or impossible because the phase becomes too thick for the rheology modifier to disperse well in the water phase, and must be added to the silicone phase. Finally, certain rheology modifiers, particularly more recently developed rheology modifiers, are more easily added to the silicone or oil phase, and doing so may make production and formulation of the silicone-in-oil compositions of the present invention more easily accomplished.

4) In a separate container, mix the water and the glycol component(s) until a uniform mixture is yielded. The combined water/glycol phase should have a refractive index near that of the silicone lubricant phase.

5) Add a small amount of water (5 to 20% of the total weight of the composition), or add a small amount (5-20%) of the mixed water/glycol phase, to the silicone lubricant phase and mix gently for a sufficient time to create a water-in-silicone emulsion.

6) Add the water/glycol phase (or the remaining water/glycol phase) to the silicone lubricant phase slowly and with sufficient agitation to invert the water-in-oil emulsion to a silicone-in-water emulsion.

7) Adjust the refractive index of the water-glycol aqueous phase, if necessary, to substantially match the refractive index of the silicone lubricant phase.

Another exemplary method of making a product in accordance with the present invention is as follows:

a) mix, in a first vessel, at least one silicone lubricant component with at least one non-ionic surfactant emulsifier component at a temperature at least equal to the melting point of the component having the highest melting point, to form a uniform silicone phase;

b) mix, in a second vessel, water and a glycol component having a refractive index higher than that of water to form a uniform aqueous phase;

c) mix to uniformity a rheology modifier with either the silicone phase or the aqueous phase;

d) gently mix with the silicone phase from about 5% to about 20%, by weight of the final composition, of an aqueous component selected from the group consisting of water and an aliquot of the aqueous phase, until a water-in-silicone emulsion is formed;

e) slowly add the aqueous phase, or the remaining aqueous phase, to the silicone phase with sufficient agitation to invert the emulsion to a silicone-in-water emulsion; and f) titrate, if necessary, a refractive index adjusting agent into the silicone-in-water emulsion until the composition is clear or translucent.

Examples 2-7

The formulations shown below in Table 2 were made according to the methods described in Example 1.

TABLE 2

| INGREDIENT | EX2 wt % | EX3 wt % | EX4 wt % | EX5 wt % | EX6 wt % | EX7 wt % |
|---|---|---|---|---|---|---|
| Component A | | | | | | |
| CRL-3932 | 25.0 | 30.0 | 30.0 | 35.0 | 40.0 | 25 |
| EMT-10 | 0.4 | 0.3 | 0.2 | 0.3 | 0.3 | 0.3 |
| Laureth 4 | 2.0 | | | 3.0 | 3.0 | |
| Laureth 24 | 2.0 | | | 3.0 | 3.0 | |
| Deceth-5 | | 3.0 | 3.0 | | | 2.0 |
| Ceteareth-25 | | 3.0 | 3.0 | | | 2.0 |
| Component B | | | | | | |
| DI water | 10.0 | 10.0 | 10.0 | 10.0 | 10.0 | 10.0 |
| Component C | | | | | | |
| DI water | 25.5 | 18.6 | 20.2 | 13.6 | 8.6 | 27.1 |
| PEG 90M | 0.1 | 0.1 | | 0.1 | 0.1 | |
| PEG-8 | 35.0 | 35.0 | 35.0 | 35.0 | 35.0 | |
| Butylene glycol | | | | | | 33.6 |
| Component D | | | | | | |
| DI water (if necessary) | qs to clear | qs to clear | qs to clear | qs to clear | qs to clear | qs to clear |
| PEG-4 (if necessary) | qs to clear | qs to clear | qs to clear | qs to clear | qs to clear | qs to clear |
| Viscosity (cps) | 600 | 738 | 462 | 800 | 946 | 540 |

Each of these final formulations is a clear and stable personal lubricant composition and non-irritating to sensitive skin, such as vaginal, penile and anal tissue and mucosa.

Examples 8-10

The formulations shown below in Table 3 were made according to the methods described in Example 1.

TABLE 3

| Ingredient | EX8 wt % | EX9 wt % | EX10 wt % |
|---|---|---|---|
| Component A | | | |
| CRL-3932 | 30.0 | 30.0 | 25 |
| EMT-10 | 0.2 | 0.2 | 0.3 |
| Laureth 4 | 2.5 | 3.0 | 2.0 |
| Laureth 24 | 2.5 | 3.0 | 2.0 |
| Component B | | | |
| DI water | 10.0 | 10.0 | 10.0 |
| Component C | | | |
| DI water | 14.8 | 13.8 | 18.7 |
| Butylene glycol | 40.0 | 40.0 | 42.0 |
| Component D | | | |
| DI water | qs to clear | qs to clear | qs to clear |
| Butylene Glycol | qs to clear | qs to clear | qs to clear |
| Viscosity (cps) | 350 | 460 | 540 |

Each of these final formulations is a clear and stable personal lubricant composition and non-irritating to sensitive skin, such as vaginal, penile and anal tissue and mucosa.

Examples 11-15

The formulations shown below in Table 4 were made according to the methods described in Example 1.

TABLE 4

| Ingredients | EX11 wt % | EX12 wt % | EX13 wt % | EX14 wt % | EX15 wt % |
|---|---|---|---|---|---|
| Component A | | | | | |
| CF 7007-DM | 30.0 | 25.0 | | | |
| CF 2002-OH | | | 30.0 | 25.0 | 30.00 |
| EMT-10 | 0.3 | 0.3 | | 0.3 | 0.30 |
| Laureth 4 | 3.0 | 2.0 | | 2.0 | 2.50 |
| Laureth 24 | 3.0 | 2.0 | | 2.0 | 2.50 |
| Deceth-5 | | | 2.5 | | |
| Ceteareth-25 | | | 2.5 | | |
| Component B | | | | | |
| DI water | 10.0 | 10.0 | 10.0 | 10.0 | 10.00 |
| Component C | | | | | |
| DI water | 14.7 | 18.7 | 14.7 | 18.7 | 14.70 |
| Hydroxypropyl Methyl cellulose | | | 0.25 | | |
| Butylene glycol | 39.0 | 42.0 | 40.0 | 42.0 | 40.00 |
| Component D | | | | | |
| DI water | qs to clear | qs to clear | qs to clear | qs to clear | qs to clear |
| PEG-4 | qs to clear | qs to clear | qs to clear | qs to clear | qs to clear |
| Viscosity (cps) | 1380 | 610 | 1100 | 610 | 460 |
| | 100.0 | 100.0 | 100.0 | 100.0 | 100.0 |

Each of these final formulations is a clear and stable personal lubricant composition and non-irritating to sensitive skin, such as vaginal, penile and anal tissue and mucosa.

Examples 16-20

The formulations shown below in Table 5 were made according to the methods described in Example 1.

TABLE 5

| Ingredients | EX16 wt % | EX17 wt % | EX18 wt % | EX19 wt % | EX20 wt % |
|---|---|---|---|---|---|
| Component A | | | | | |
| CF 0515-OH | 30.0 | 25.0 | 30.0 | 25.0 | 30.00 |
| EMT-10 | 0.3 | 0.3 | | 0.3 | 0.30 |
| C12-13 Pareth-3 | 3.0 | 2.0 | | 2.0 | 2.50 |
| C12-13 Pareth-23 | 3.0 | 2.0 | | 2.0 | 2.50 |
| Deceth-5 | | | 2.5 | | |
| Ceteareth-25 | | | 2.5 | | |
| Component B | | | | | |
| DI water | 10.0 | 10.0 | 10.0 | 10.0 | 10.00 |
| Component C | | | | | |
| DI water | 14.7 | 18.7 | 14.7 | 18.7 | 14.70 |
| Hydroxypropyl Methyl cellulose | | | 0.25 | | |
| PEG-4 | 39.0 | 42.0 | 40.0 | 42.0 | 40.00 |
| Component D | | | | | |
| DI water | qs to clear | qs to clear | qs to clear | qs to clear | qs to clear |
| PEG-4 | qs to clear | qs to clear | qs to clear | qs to clear | qs to clear |
| Viscosity (cps) | 1380 | 610 | 1100 | 610 | 460 |

Each of these final formulations is a clear transparent personal lubricant composition and non-irritating to sensitive skin, such as vaginal, penile and anal tissue and mucosa.

Examples 21-24

The formulations shown below in Table 6 are made according to the methods described in Example 1.

TABLE 6

| Ingredients | EX20 wt % | EX21 wt % | EX22 wt % | EX23 wt % |
|---|---|---|---|---|
| Component A | | | | |
| CF 3557-OH | 25.00 | 30.00 | 35.00 | 40.00 |
| EMT-10 | 0.30 | 0.30 | 0.25 | 0.40 |
| C12-13 Pareth-23 | 2.00 | 2.50 | 2.80 | 3.00 |
| C12-13 Pareth-4 | 2.00 | 2.50 | 2.80 | 3.00 |
| Component B | | | | |
| DI water | 10.00 | 10.00 | 10.00 | 10.00 |
| Component C | | | | |
| DI water | 17.70 | 15.70 | 12.15 | 13.00 |
| PEG-8 | 33.00 | 29.00 | 27.00 | 20.60 |
| PEG-12 | 10.00 | 10.00 | 10.00 | 10.00 |
| Component D | | | | |
| DI water | qs to clear | qs to clear | qs to clear | qs to clear |
| Glycerin | qs to clear | qs to clear | qs to clear | qs to clear |
| | 100.00 | 100.00 | 100.00 | 100.00 |

Each of these final formulations is a clear transparent personal lubricant composition and non-irritating to sensitive skin, such as vaginal, penile and anal tissue and mucosa.

To the extent that a plurality of inventions may be disclosed herein, any such invention shall be understood to have disclosed herein alone, in combination with other features or inventions disclosed herein, or lacking any feature or features not explicitly disclosed as essential for that invention. For example, the inventions described in this specification can be practiced within elements of, or in combination with, other any features, elements, methods or structures described herein. Additionally, features illustrated herein as being present in a particular example are intended, in other examples of the present invention, to be explicitly lacking from the invention, or combinable with features described elsewhere in this patent application, in a manner not otherwise illustrated in this patent application or present in that particular example. The scope of the invention shall be determined solely by the language of the claims.

Thus, the various descriptions of the invention provided herein illustrate presently preferred examples of the invention; however, it will be understood that the invention is not limited to the examples provided, or to the specific configurations and relation of elements unless the claims specifically indicate otherwise. Based upon the present disclosure a person of ordinary skill in the art will immediately conceive of other alternatives to the specific examples given, such that the present disclosure will be understood to provide a full written description of each of such alternatives as if each had been specifically described.

What is claimed is:

1. A low-viscosity, substantially clear or translucent silicone-in-water emulsion composition comprising an amount of water and,
about 0.1% to about 1% by weight of a rheology modifier,
about 1% to about 6% by weight of an emulsifier component consisting of one or more non-ionic surfactant component;
about 15% to about 60% by weight of one or more silicone lubricants present in a water-immiscible silicone phase; and
an amount of one or more water-miscible refractive index (RI) adjusting agent ("RIAA") sufficient to render the composition substantially clear or translucent; the low-viscosity, substantially clear or translucent silicone-in-water emulsion composition having an average diameter of the dispersed phase silicone droplets in the range between about 200 nm and about 500 nm and effective as a lubricant suitable for use in intimate care applications;
said low-viscosity, substantially clear or translucent silicone-in-water emulsion composition
(i) having a viscosity of 15,000 cPa or less, and
(ii) remaining stable for at least 1 year at room temperature.

2. The silicone-in-water emulsion composition of claim 1 wherein the silicone is present in silicone phase droplets having an average diameter of about 300 nm.

3. The silicone-in-water emulsion composition of claim 1 wherein the one or more silicone lubricants comprise about 15% to about 40% by weight of the composition and the RIAA comprises about 15% to about 30% by weight of the composition.

4. A condom product comprising packaging containing a condom and the composition of claim 1.

5. The low-viscosity, substantially clear or translucent silicone-in-water emulsion composition of claim 1, formulated for use as a surgical lubricant.

6. The low-viscosity, substantially clear or translucent silicone-in-water emulsion composition of claim 1, formulated for use as a skin treatment composition.

7. A pharmaceutical or cosmetic composition comprising the silicone-in-water emulsion of claim 1 and an additional pharmaceutical or cosmetically active ingredient.

8. A pharmaceutical or cosmetic composition comprising the silicone-in-water emulsion of claim 1 and an additional pharmaceutical or cosmetically active ingredient selected from the group consisting of a hormone component, an antimicrobial component, an antibacterial component, an antibiotic component, an antiviral component, a non-steroidal anti-inflammatory component, a spermicide component, an immunodilator component, an anesthetic component, a plant extract component, a vitamin component, a corticosteroid component, and an antifungal component and the like, and mixtures thereof.

9. A method of making the low-viscosity, substantially clear or translucent silicone-in-water emulsion composition of claim 1 comprising:
a) slowly adding water with gentle mixing to a silicone lubricant, at least one non-ionic surfactant component, and a hydrophilic rheology modifier to form a water-in-silicone emulsion;
b) combining water and a glycol with the viscous water-in-silicone emulsion with mixing for a sufficient time to invert the viscous water-in-silicone emulsion to a silicone-in-water emulsion; and
c) optionally adding an effective amount of a refractive index (RI) adjustment agent ("RIAA")
to obtain the low-viscosity, substantially clear or translucent silicone-in-water emulsion composition of claim 1.

10. The method of claim 9, wherein said at least one non-ionic surfactant component is selected from the group consisting of polyalkylene glycol alkyl ethers; glucoside alkyl ethers; polyethylene glycol alkylphenyl ethers, glycerol alkyl esters; polyoxyethylene glycol sorbitan alkyl esters; sorbitan alkyl esters; an alkyl polyglucoside; alkylamide ethanolamines; alkane alkylamine oxides; block copolymers of polyethylene glycol and polypropylene glycol; polyethoxylated fatty acid amines; and ethoxylated aliphatic alcohols.

11. The method of claim 9 wherein the at least one non-ionic surfactant comprises two different non-ionic surfactant components.

12. The method of claim 9 wherein the at least one non-ionic surfactant comprises two different fatty alcohol ethoxylate surfactant components present in an effective amount of about 1% to about 6% by weight of the silicone-in-water emulsion.

13. The method of claim 9, wherein the rheology modifier is present in an effective amount of about 0.1% to about 1% by weight of the silicone-in-water emulsion.

14. The method of claim 11, wherein said at least one non-ionic surfactant component comprises at least one of (A) a first polymeric material made from a polyoxyethylene alkyl alcohol containing from 2 to 12 ethylene glycol units and (B) a second polymeric material made from a polyoxyethylene alkyl alcohol containing from 12 to 100 ethylene glycol units.

15. The method of claim 14, wherein said one non-ionic surfactant component comprises a first ethoxylated lauryl alcohol, containing 4 ethylene glycol units; and a second ethoxylated lauryl alcohol containing 23 ethylene glycol units.

16. The method of claim 14 wherein at least one of (A) and (B) is present in an amount of about 1% to about 6% by weight of the silicone-in-water emulsion.

17. The method of claim 9, wherein the RIAA is supplied so that the silicone-in-water emulsion includes about 1% by weight to about 40% by weight of the RI adjustment agent.

18. A low-viscosity, substantially clear or translucent silicone-in-water emulsion composition comprising a water phase and a water-immiscible silicone phase, comprising:
about 15% to about 60% by weight of one or more silicone lubricants;
about 1% to about 6% by weight of an emulsifier component comprising at least one non-ionic surfactant;
about 0.1% to about 0.8% by weight of a rheology modifier component;
a sufficient quantity of one or more water-soluble refractive index adjusting agent ("RIAA") other than water to cause the refractive index of the water phase to substantially match the refractive index of the silicone phase of the composition; and
water in a sufficient quantity so that the composition totals 100% by weight, the low-viscosity, substantially clear or translucent silicone-in-water emulsion composition
(i) having an average diameter of the dispersed phase silicone droplets in the range between about 200 nm and about 500 nm,
(ii) having a viscosity of 15,000 cPa or less, (iii) remaining stable for at least 1 year at room temperature, and
(iv) being suitable for use as a lubricant in one or more intimate care applications.

19. The emulsion of claim 18 wherein the sufficient quantity of one or more RIAA is in the range of about 10% to about 40% by weight of the composition.

20. The emulsion of claim 18 wherein the emulsion has an average silicone phase droplet size of about 300 nanometers.

21. The low-viscosity, substantially clear or translucent silicone-in-water emulsion composition of claim 18, formulated by:
   a) slowly adding water with gentle mixing to a silicone lubricant and an emulsifier component consisting of one or more non-ionic surfactant component to form a water-in-silicone emulsion;
   b) combining water and a glycol with the viscous water-in-silicone emulsion with gentle mixing for a sufficient time to invert the viscous water-in-silicone emulsion to a silicone-in-water emulsion;
   c) wherein a hydrophilic rheology modifier is added at either step a) or step b);
   d) optionally adding an effective amount of a refractive index (RI) adjustment agent ("RIAA") to the stable, low viscosity, silicone-in-water lubricant emulsion composition;
to obtain said low-viscosity, substantially clear or translucent silicone-in-water emulsion composition of claim 18.

\* \* \* \* \*